United States Patent
Kamal et al.

(10) Patent No.: US 9,108,960 B2
(45) Date of Patent: Aug. 18, 2015

(54) NITROFURFURYL SUBSTITUTED PHENYL LINKED PIPERIDINO-OXADIAZOLINE CONJUGATES AS ANTI-TUBERCULAR AGENTS AND PROCESS FOR THE PREPARATION THEREOF

(71) Applicant: Council Of Scientific & Industrial Research, New Delhi (IN)

(72) Inventors: Ahmed Kamal, Hyderabad (IN); Arutla Viswanath, Hyderabad (IN); Jayanti Naga Srirama Chandra Murty, Hyderabad (IN); Farheen Sulthana, Hyderabad (IN); Gadupudi Ramakrishna, Hyderabad (IN); Inshad Ali Khan, Hyderabad (IN); Nitin Pal Kalia, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/367,602

(22) PCT Filed: Dec. 18, 2012

(86) PCT No.: PCT/IN2012/000827
§ 371 (c)(1),
(2) Date: Jun. 20, 2014

(87) PCT Pub. No.: WO2013/093940
PCT Pub. Date: Jun. 27, 2013

(65) Prior Publication Data
US 2014/0336388 A1 Nov. 13, 2014

(30) Foreign Application Priority Data
Dec. 20, 2011 (IN) .............................. 3731/DEL/2011

(51) Int. Cl.
*C07D 413/14* (2006.01)
*C07D 413/12* (2006.01)

(52) U.S. Cl.
CPC ............ *C07D 413/14* (2013.01); *C07D 413/12* (2013.01)

(58) Field of Classification Search
CPC ..................................................... C07D 413/14
USPC ........................................................ 546/209
See application file for complete search history.

(56) References Cited

U.S. PATENT DOCUMENTS

2005/0026968 A1 * 2/2005 Lee et al. ...................... 514/363

FOREIGN PATENT DOCUMENTS

WO 2005007625 A2 1/2005
WO 2005007625 A3 1/2005
WO WO2012/123971 * 9/2012

OTHER PUBLICATIONS

Horvati et al. "Enhanced cellular uptake . . . " Bioconjugate Chem. 23(5) 900-907 (2012).*
Rakesh et al. "Antitubercular nitrofuran . . . " Bioorg, Med. Chem. 20(20) 6063-6072 (2012).*
Tangallapally et al. "Discovery of novel isoxazolines . . . " Bioorg. Med. Chem. Lett. 17(23) 6638-6642 (2007).*
International Searching Authority, International Search Report and Written Opinion in corresponding Application No. PCT/IN2012/000827, mailed Mar. 1, 2013 (9 pages).
Mamolo, Maria Grazia, et al., Antimycobacterial Activity of New 3-substituted 5-(pyridin-4-yl-)3H-1,3,4-oxadiazol-2-one and 2-thione Derivatives. Preliminary Molecular Modeling Investigations, Bioorganic & Medicinal Chemistry, Jun. 1, 2005, pp. 3797-3809, vol. 13, No. 11, Elsevier, Pergamon, Great Britain.
Budha, Nageshwar R., et al., Pharmacokinetically-Guided Lead Optimization of Nitrofuranylamide Anti-Tuberculosis Agents, The American Association of Pharmaceutical Scientists Journal, Mar. 2008, pp. 157-165, vol. 10, No. 1.
Rakesh, Dianqing Sun, et al., Synthesis, Optimization and Structure-Activity Relationships of 3, 5-Disubstituted Isoxazolines as New Anti-Tuberculosis Agents, European Journal of Medicinal Chemistry, Feb. 1, 2009, pp. 460-472, vol. 44, No. 2, Elsevier, Paris, France.
Kamal, Ahmed, et al., Antitubercular Agents. Part 1: Synthesis of Phthalimido- and Naphthalimido-Linked Phenazines as New Prototype Antitubercular Agents, Bioorganic & Medicinal Chemistry Letters, 2005, pp. 1923-1926, issue 15, Elsevier.

(Continued)

*Primary Examiner* — Celia Chang
(74) *Attorney, Agent, or Firm* — Wood, Herron, Evans, LLP

(57) ABSTRACT

The present invention provides nitrofurfuryl substituted phenyl linked piperidino-oxadiazolone compounds of general formula (A) as anti-tubercular agents; wherein G=formula (B); X=H, F; R=H, $CH_3$, $C_2H_5$, Benzyl.

9 Claims, 1 Drawing Sheet (56) References Cited

OTHER PUBLICATIONS

Kamal, Ahmed, et al., Anti-Tubercular Agents. Part 3: Benzothiadiazine as a Novel Scaffold for Anti-Mycobacterium Activity, Bioorganic & Medicinal Chemistry Letters, 2006, pp. 650-658, issue 14, Elsevier.

Kamal, Ahmed, et al., Anti-Tubercular Agents. Part IV: Synthesis and Antimycobacterial Evaluation of Nitroheterocyclic-Based 1,2,4-Benzothiadiazines, Bioorganic & Medicinal Chemistry Letters, 2007, pp. 5419-5422, issue 17, Elsevier.

Kamal, Ahmed, et al., Anti-Tubercular Agents. Part 5: Synthesis and Biological Evaluation of Benzothiadiazine 1,1-Dioxide Based Congeners, European Journal of Medicinal Chemistry, 2010, pp. 4545-4553, issue 45, Elsevier.

Tangallapally, Rajendra P., et al., Synthesis and Evaluation of Nitrofuranylamides as Novel Antituberculosis Agents, Journal of Medicinal Chemistry, 2004, pp. 5276-5283, vol. 47, No. 21, American Chemical Society.

Tangallapally, Rajendra P., et al., Synthesis and Evaluation of Cyclic Secondary Amine Substituted Phenyl and Benzyl Nitrofuranyl Amides as Novel Antituberculosis Agents, Journal of Medicinal Chemistry, 2005, pp. 8261-8269, vol. 48, No. 26, American Chemical Society.

Hurdle, Julian G., et al., A Microbiological Assessment of Novel Nitrofuranylamides as Anti-Tuberculosis Agents, Journal of Antimicrobial Chemotherapy, 2008, pp. 1037-1045, vol. 62, Oxford University Press.

\* cited by examiner

Scheme: 1

NITROFURFURYL SUBSTITUTED PHENYL LINKED PIPERIDINO-OXADIAZOLINE CONJUGATES AS ANTI-TUBERCULAR AGENTS AND PROCESS FOR THE PREPARATION THEREOF

FIELD OF THE INVENTION

The present invention relates to the nitrofurfuryl substituted phenyl linked piperidino-oxadiazolone compounds of general formula A and a process for the preparation thereof. The present invention further relates to the pharmaceutically acceptable salts of nitrofurfuryl substituted phenyl linked piperidino-oxadiazolone compounds of general formula A useful as potential anti-tubercular agents General formula A Wherein

X = H or F;
R = H, CH₃, C₂H₅ or —CH₂C₆H₅;

The structural formula of the representative group of nitrofurfuryl substituted phenyl linked piperidino-oxadiazolone compounds are given below:

Formula 8a-h

X = H, F;
R = H, CH₃, C₂H₅, CH₂C₆H₅;

Formula 9a-h

X = H, F;
R = H, CH₃, C₂H₅, CH₂C₆H₅;

Formula 10a-h

X = H, F;
R = H, CH₃, C₂H₅, CH₂C₆H₅;

BACKGROUND OF THE INVENTION

Someone in the world is newly infected with tuberculosis (TB) bacilli every second. Overall one-third of the world's population is currently infected with tuberculosis and it has been estimated that 5-10% of those people are expected to become sick or infectious at some point in their lifetime. The major challenges for tuberculosis control are the development of multidrug-resistant tuberculosis (MDR-TB) strains and the increasing numbers of immunocompromised individuals with HIV infections who are highly susceptible to the disease. No new effective treatments have been developed since the introduction of Rifampicin in 1971, even though there have been significant advances in drug development technologies. Consequently there is an urgent need to develop new, potent, fast-acting anti-tubercular drugs with low-toxicity profiles that can be used in conjunction with drugs used to treat HIV infections.

As a part of investigation of new chemotherapeutic agents from this laboratory, over the past eight years our research efforts have been focused towards the intervention of new scaffolds with good anti-mycobacterial activity and eventually to develop new anti-tubercular agents that can improve the current therapeutic regimen as well as effective in the treatment of MDR-TB (Kamal, A.; Babu, A. H.; Ramana, A. V.; Sinha, R.; Yadav, J. S.; Arora, S. K. *Bioorg. Med. Chem. Lett.* 2005, 15, 1923-1926.; Kamal, A.; Reddy, K. S.; Ahmed, S. K.; Khan, M. N. A.; Sinha, R. K.; Yadav, J. S.; Arora, S. K. *Bioorg. Med Chem.* 2006, 14, 650-658.; Kamal, A.; Ahmed, S. K.; Reddy, K. S.; Khan, M. N. A.; Shetti, R. V. C. R. N. C.; Siddhardha, B.; Murthy, U. S. N.; Khan, I. A.; Kumar, M.; Sharma, S.; Ram, A. B. *Bioorg. Med. Chem. Lett.* 2007, 17, 5419-5422; Kamal, A.; Azeeza, S.; Malik, M. S.; Faazil, S. *Int. J. of Medical and Biological Frontiers* 2010, 16, 535-568.; Kamal, A.; Shetti, R. V. C. R. N. C.; Azeeza, S.; Ahmed, S. K.; Swapna, P.; Malla Reddy, A.; Khan, I. A.; Sharma, S.; Abdullah, S. T.; *Eur. J. of Med. Chem.* 2010, 45, 4545-4553).

Nitrofuranylamides compounds (11(a-c)) that have been discovered recently and showed potent anti-tuberculosis activity (Huedle, J. G.; Budha, N. R.; Carson, E. I.; Qi, J.; Scherman, M. S.; Cho, S. H.; McNeil, M. R.; Lenaerts, A. J.; Franzblau, S. G.; Meibohm, B.; Lee, R. E. J. *Antimicro. Chemother.* 2008, 62 1037-1045). Nitrofuranyl amide compounds exhibited good thearapeutic value. They are members of an emerging new class of nitroaromatic antibiotics that are currently being intensively investigated as new anti-tuberculosis drugs. (Tangallapally, R. P.; Yendapally, R; Lee, E. R.; Lenaerts, A. J. M.; and Lee, R. E. *J. Med. Chem.*, 2005, 48, 8261-8269); Tangallapally, R, P.; Yendapally, R.; Lee, R. E.; Hevener, K.; Jones, V. C.; Lenaerts, A. J. M.; McNeil, M. R.; Wang, Y.; Franzblau, S.; Lee, R. E. *J. Med. Chem.*, 2004, 47, 5276-5283).

Oxadiazalone (12(ac)) are a class of compounds comprising anti-tubercular activity and they showed interesting activity (Mamolo, M. G.; Zampieri, D.; Vio, L.; Fermeglia, m.; Ferrone, M.; Pricl, S; Scialino, G. and Banfi, E. *Bioorg. Med. Chem.*, 2005, 13, 3797-3809).

Figure 1:
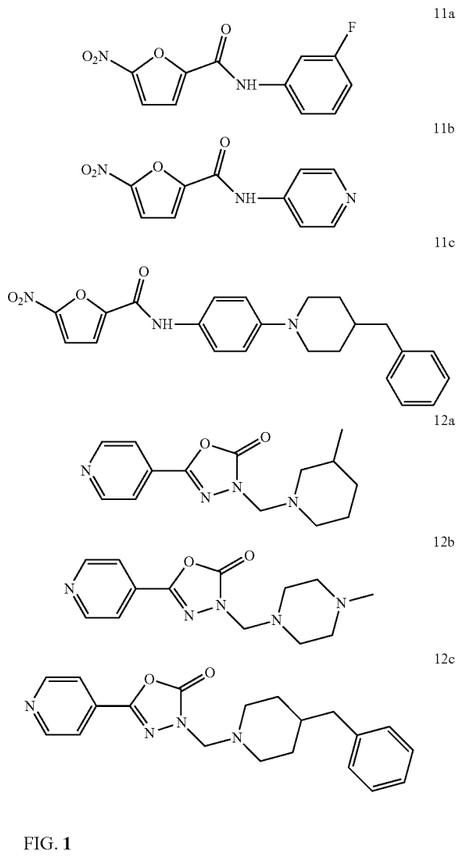

FIG. 1 represents structural formula of the compounds: N2-(3-fluorophenyl)-5-nitro-2-furamide (11a), N2-(4-pyridyl)-5-nitro-2-furamide (11b), N2-[4-(4-benzylpiperidino) phenyl]-5-nitro-2-furamide (11c), 3-[(3-methylpiperidino) methyl]-5-(4-pyridyl)-2,3-dihydro-1,3,4-oxadiazol-2-one (12a), 3-[(4-methylpiperazino)methyl]-5-(4-pyridyl)-2,3-dihydro-1,3,4-oxadiazol-2-one (12b), 3-[(4-benzylpiperidino) methyl]-5-(4-pyridyl)-2,3-dihydro-1,3,4-oxadiazol-2-one (12c).

FIG. 1

Keeping this aspect in mind, nitrofurfuryl substituted phenyl linked piperidino-oxadiazolone compounds were designed and synthesized.

Objectives of the Invention

The main objective of the present invention is to provide nitrofurfuryl substituted phenyl linked piperidino-oxadiazolone compounds of general formula A useful as anti-tubercular agent.

Another objective of the present invention is to provide process for the preparation of nitrofurfuryl substituted phenyl linked piperidino-oxadiazolone compounds of general formula A.

SUMMARY OF THE INVENTION

Accordingly, the present invention provides a compound of general formula A or pharmaceutically acceptable salts thereof In one embodiment of the present invention, the chemical formula of the representative compounds are:

N2-4-[4-(5-oxo-4,5-dihydro-1,3,4-oxadiazol-2-yl)piperidino]phenyl-5-nitro-2-furamide (8a);

N2-4-[4-(4-Methyl-5-oxo-4,5-dihydro-1,3,4-oxadiazol-2-yl)piperidino]phenyl-5-nitro-2-furamide (8b);

N2-4-[4-(4-Ethyl-5-oxo-4,5-dihydro-1,3,4-oxadiazol-2-yl)piperidino]phenyl-5-nitro-2-furamide (8c);

N2-4-[4-(4-Benzyl-5-oxo-4,5-dihydro-1,3,4-oxadiazol-2-yl)piperidino]phenyl-5-nitro-2-furamide (8d);

N2-3-Fluoro-4-[4-(5-oxo-4,5-dihydro-1,3,4-oxadiazol-2-yl)piperidino]phenyl-5-nitro-2-furamide (8e);

N2-3-Fluoro-4-[4-(4-methyl-5-oxo-4,5-dihydro-1,3,4-oxadiazol-2-yl)piperidino]phenyl-5-nitro-2-furamide (8f);

N2-4-[4-(4-Ethyl-5-oxo-4,5-dihydro-1,3,4-oxadiazol-2-yl)piperidino]-3-fluorophenyl-5-nitro-2-furamide (8g);

N2-4-[4-(4-Benzyl-5-oxo-4,5-dihydro-1,3,4-oxadiazol-2-yl)piperidino]-3-fluorophenyl-5-nitro-2-furamide (8h);

5-[1-(4-[(E)-1-(5-Nitro-2-furyl)methylidene]aminophenyl)-4-piperidyl]-2,3-dihydro-1,3,4-oxadiazol-2-one (9a);

3-Methyl-5-[1-(4-[(E)-1-(5-nitro-2-furyl)methylidene]aminophenyl)-4-piperidyl]-2,3-dihydro-1,3,4-oxadiazol-2-one (9b);

3-Ethyl-5[1-(4-[(E)-1-(5-nitro-2-furyl)methylidene]aminophenyl)-4-piperidyl]-2,3-dihydro-1,3,4-oxadiazol-2-one (9c);

3-Benzyl-5-[1-(4-[(E)-1-(5-nitro-2-furyl)methylidene]aminophenyl)-4-piperidyl]-2,3-dihydro-1,3,4-oxadiazol-2-one (9d);

5-[1-(2-Fluoro-4-[(E)-1-(5-nitro-2-furyl)methylidene]aminophenyl)-4-piperidyl]-2,3-dihydro-1,3,4-oxadiazol-2-one (9e);

5-[1-(2-Fluoro-4-[(E)-1-(5-nitro-2-furyl)methylidene]aminophenyl)-4-piperidyl]-3-methyl-2,3-dihydro-1,3,4-oxadiazol-2-one (9f);

3-Ethyl-5-[1-(2-fluoro-4-[(E)-1-(5-nitro-2-furyl)methylidene]aminophenyl)-4-piperidyl]-2,3-dihydro-1,3,4-oxadiazol-2-one (9g);

3-Benzyl-5-[1-(2-fluoro-4-[(E)-1-(5-nitro-2-furyl)methylidene]aminophenyl)-4-piperidyl]-2,3-dihydro-1,3,4-oxadiazol-2-one (9h);

5-[1-(4-[(5-Nitro-2-furyl)methyl]aminophenyl)-4-piperidyl]-2,3-dihydro-1,3,4-oxadiazol-2-one (10a);

3-Methyl-5-[1-(4-[(5-nitro-2-furyl)methyl]aminophenyl)-4-piperidyl]-2,3-dihydro-1,3,4-oxadiazol-2-one (10b);

3-Ethyl-5-[1-(4-[(5-nitro-2-furyl)methyl]aminophenyl)-4-piperidyl]-2,3-dihydro-1,3,4-oxadiazol-2-one (10c);

3-Benzyl-5-[1-(4-[(5-nitro-2-furyl)methyl]aminophenyl)-4-piperidyl]-2,3-dihydro-1,3,4-oxadiazol-2-one (10d);

5-[1-(2-Fluoro-4-[(5-nitro-2-furyl)methyl]aminophenyl)-4-piperidyl]-2,3-dihydro-1,3,4-oxadiazol-2-one (10e);

5-[1-(2-Fluoro-4-[(5-nitro-2-furyl)methyl]aminophenyl)-4-piperidyl]-3-methyl-2,3-dihydro-1,3,4-oxadiazol-2-one (10f);

3-Ethyl-5-[1-(2-fluoro-4-[(5-nitro-2-furyl)methyl]aminophenyl)-4-piperidyl]-2,3-dihydro-1,3,4-oxadiazol-2-one (10g);

3-Benzyl-5-[1-(2-fluoro-4-[(5-nitro-2-furyl)methyl]aminophenyl)-4-piperidyl]-2,3-dihydro-1,3,4-oxadiazol-2-one (10h);

In another embodiment of the present invention, the structural formula of the representative compounds are

8a

8b

8c

8d

8e

8f

8g

8h

9a

9b

9c

9d

In still another embodiment of the present invention, the compounds of the general formula A or pharmaceutically acceptable salts thereof are useful as anti-tuberculosis agent.

In yet another embodiment of the present invention, the compounds of the general formula A exhibiting MIC in the range of 0.5 to 4 (μg/ml), 1 to 8 (μg/ml), 2 to 16 (μg/ml), against *Mycobacterium tuberculosis* H37Rv, *Mycobacterium tuberculosis* Rif$^R$, *Mycobacterium tuberculosis* XDR-1 respectively at an exposure period 3-4 days.

In still another embodiment of the present invention provides a process for the preparation of the compounds of general formula A or pharmaceutically acceptable salts thereof, comprising the steps of:

i. heating methyl 4-piperidinecarboxylate (2) with compounds of general formula 1(a-b) in dimethylsulphoxide and in the presence of base selected from $K_2CO_3$ or $Na_2CO_3$ for a period in the range of 8 to 10 h at temperature ranging between 70 to 80° C. to obtain compound of general formula 3(a-b)

1a X = H, 1b X = F

2 ii. treating the compounds of general formula 3(a-b) as obtained in step (i.) with $NH_2NH_2.H_2O$ in solvent selected from ethanol or 2-propanol under refluxing temperature ranging between 65 to 70° C. for a period in the range of 12 to 24 h to obtain hydrazide of general formula 4(a-b), 4(a-b)

4a X = H,
4b X = F iii. adding N,N-dimethylcarbamylchloride to hydrazide 4(a-b) as obtained in step (ii) in pyridine at temperature ranging between 25 to 27° C. and followed by refluxing at temperature ranging between 85 to 90° C. for 2 to 3 h to obtain the compounds of general formula 5(a-b).

5(a-b)

5a X = H
5b X = F iv. reacting the compound of general formula 5(a-b) with halides selected from alkyl halides or benzyl bromide in N,N-dimethylformamide (DMF) at a temperature ranging between 25° C. to 27° C. for a period in the range of 10 to 12 h or in acetone at refluxing temperature in the range of 65 to 70° C. for 12 to 24 h to obtain the compounds of general formula 6(a-f).

6(a-f)

X = H, F; R = $CH_3$, $C_2H_5$, $CH_2C_6H_5$;
6a X = H, R = $CH_3$;
6b X = H, R = $C_2H_5$;
6c X = H, R = $CH_2C_6H_5$;
6d X = F, R = $CH_3$;
6e X = F, R = $C_2H_5$;
6f X = F, R = $CH_2C_6H_5$ v. reducing the compound of general formula 5(a-b) as obtained in step (iii) or 6(a-f) as obtained in step iv by $SnCl_2.2H_2O$ or Fe powder and two drops of conc HCl in methanol at refluxing temperature in the range of 65 to 70° C. for a period in the range of 4 to 6 h or Znic in acetic acid at room temperature (25 to 27° C.) for 4 to 5 h to obtain the compound of general formula 7(a-h).

7(a-h)

X = H, F; R = H, $CH_3$, $C_2H_5$, $CH_2C_6H_5$;
7a X = H, R = H;
7b X = H, R = $CH_3$;
7c X = H, R = $C_2H_5$;
7d X = H, R = $CH_2C_6H_5$;
7e X = F, R = H;
7f X = F, R = $CH_3$;
7g X = F, R = $C_2H_5$;
7h X = F, R = $CH_2C_6H_5$;

vi. reacting the compound of general formula 7(a-h) with 5-nitro-2-furanoic acid, 1-Ethyl-3-(3-dimethylaminopropyl)carbodiimide) (EDCI) and Hydroxybenzotriazole (HOBT) in N,N-dimethylformamide (DMF) at temperature ranging between 25° C. to 27° C. for a period ranging between 3 to 4 h to obtain compound of general formula 8 (a-h), 8(a-h)

X = H, F; R = H, $CH_3$, $C_2H_5$, Bn;

vii. reacting the compound of general formula (7a-h) with 5-nitro-2-furaldehyde in the presence of catalytic amount of acid selected from $CH_3COOH$ or $H_2SO_4$ in solvent selected from methanol or ethanol at a temperature ranging between 0° C. to 5° C. for a period in the range of 10 to 12 h to obtain the compounds of general formula 9(a-h),

9(a-h)

X = H, F; R = H, CH$_3$, C$_2$H$_5$, CH$_2$C$_6$H$_5$;

viii. reducing the compound general formula (9a-h) by reducing agent selected from sodium cyanoborohydride, or sodium triacetoxyborohydride in the presence of catalytic amount of CH$_3$COOH in solvent selected from methanol or ethanol at a temperature ranging between 0 to 5° C. for a period in the range of 10 to 12 h to obtain the compounds of general formula (10(a-h).

10(a-h)

X = H, F; R = H, CH$_3$, C$_2$H$_5$, CH$_2$C$_6$H$_5$;

ix. purifying the compounds of general formula 8(a-h) to 10(a-h) as obtained in step vi, vii and viii by column chromatography to obtain the compounds of general formula A.

In still another embodiment of the present invention, solvent used in the process step (ix) are selected from the group consisting of ethyl acetate, hexane, chloroform or methanol.

In a further embodiment of the present invention wherein the pharmaceutically acceptable salt of the compound of general formula A is selected form a group consisting of hydrochloride, hydrobromide, tartarate, succinate, maleate.

In a still further embodiment of the present invention wherein the representative pharmaceutically acceptable salt of the compound of general formula A comprising:

5-(1-(4-(1-((5-nitro-2-furyl)methyl)ammonio)phenyl)-4-piperidyl)-2,3-dihydro-1,3,4-oxadiazol-2-one chloride 3-methyl-5-(1-(4-(1-((5-nitro-2-furyl)methyl)ammonio)phenyl)-4-piperidyl)-2,3-dihydro-1,3,4-oxadiazol-2-one chloride 3-ethyl-5-(1-(4-(1-((5-nitro-2-furyl)methyl)ammonio)phenyl)-4-piperidyl)-2,3-dihydro-1,3,4-oxadiazol-2-one chloride 3-benzyl-5-(1-(4-(1-((5-nitro-2-furyl)methyl)ammonio)phenyl)-4-piperidyl)-2,3-dihydro-1,3,4-oxadiazol-2-one chloride 5-(1-(2-fluoro-4-(1-((5-nitro-2-furyl)methyl)ammonio)phenyl)-4-piperidyl)-2,3-dihydro-1,3,4-oxadiazol-2-one chloride 5-(1-(2-fluoro-4-(1-((5-nitro-2-furyl)methyl)ammonio)phenyl)-4-piperidyl)-3-methyl-2,3-dihydro-1,3,4-oxadiazol-2-one chloride 3-ethyl-5-(1-(2-fluoro-4-(1-((5-nitro-2-furyl)methyl)ammonio)phenyl)-4-piperidyl)-2,3-dihydro-1,3,4-oxadiazol-2-one chloride 3-benzyl-5-(1-(2-fluoro-4-(1-((5-nitro-2-furyl)methyl)ammonio)phenyl)-4-piperidyl)-2,3-dihydro-1,3,4-oxadiazol-2-one chloride.

BRIEF DESCRIPTION OF THE DRAWINGS

Scheme 1 represent schematic diagram for the preparation of compound of general formula 1 wherein reagent and conditions are (i) DMSO, K$_2$CO$_3$, 80° C.; 8 h; (ii) NH$_2$NH$_2$.H$_2$O, ethanol, reflux, 24 hr; (iii) (CH$_3$)$_2$NCOCl, pyridine, 80° C., 2.5 h; (iv) RBr, DMF, K$_2$CO$_3$, 27° C., 12 h; (v) SnCl$_2$.2H$_2$O, MeOH, reflux, 4 h; (vi) 5-nitro 2-furoicacid, EDCI, HOBT, DMF, 27° C., 2 h; (vii) 5-nitro 2-furaldehyde, CH$_3$COOH (cat.), MeOH, 0° C., 12 hr; (viii) sodium cyanoborohydride, CH$_3$COOH (cat.), MeOH, 0° C., 10 hr.

DETAILED DESCRIPTION OF THE INVENTION

Nitrofurfuryl substituted phenyl linked piperidino-oxadiazolone compounds have shown promising anti-tubercular activity. The molecules synthesized are of immense biological significance with potential anti-tubercular activity. This resulted in design and synthesis of new congeners as illustrated in Scheme-1, which comprise:

1. Aromatic nucleophilic substitution substituted 4-fluoro nitrobenzene with methyl 4-piperidinecarboxylate
2. Conversion of ester into their corresponding hydrazides using NH$_2$NH$_2$.H$_2$O in ethanol at refluxing conditions for 12 to 24 h.
3. Oxadiazalone ring formation takes place in the presence of dimethylcarbamyl chloride in pyridine at refluxing conditions for 2.5 h.
4. Reaction of alkyl halide and benzyl halide with oxadiazalone with K$_2$CO$_3$ in DMF.
5. Reduction of nitro group of oxadiazolone by SnCl$_2$.2H$_2$O in methanol to form amine compound.
6. Coupling reaction between oxadiazolone and 5-nitro2-furanoic acid
7. Formation of schiff's base between oxadiazolone and 5-nitro2-furaldehyde.
8. Reduction of schiff's base with sodium cyanoborohydride
9. Purification by column chromatography using different solvents like ethyl acetate, hexane, chloroform and methanol.

EXAMPLES

Following examples are given by way of illustration therefore should not be construed to limit the scope of the invention.

Example 1

N2-4-[4-(5-Oxo-4,5-dihydro-1,3,4-oxadiazol-2-yl) piperidino]phenyl-5-nitro-2-furamide (8a)

To a stirred solution of 4-fluoro nitrobenzene (1a, 3.1 g, 22 mmol) and methyl 4-piperidine carboxylate (2, 3.15 g, 22 mmol) in DMF solvent and K$_2$CO$_3$ (7.6 g, 55 mmol) as base and heated at 80° C. for 10 h, after completion of the reaction, reaction is poured into ice water and extracted into ethyl acetate finally purification by column chromatography to afford pure compound methyl 1-(4-nitrophenyl)-4-piperidinecarboxy-late (3a, 4.93 g, 85%). To a stirred solution of ester (3a, 4.75 g, 18 mmol) in ethanol, NH$_2$NH$_2$. H$_2$O (2.25 g, 45 mmol) is added and refluxed for 24 h. After completion of the reaction ethanol is evaporated under vacuum and water is added and extracted into ethyl acetate finally purification by column chromatography to afford pure compound 1-(4-nitrophenyl)-4-piperidinecarbohydrazide (4a, 3.99 g, 84%). Addition N,N-dimethyl carbamyl chloride (1.29 g, 12 mmol) to hydrazide (4a, 3.17 g, 12 mmol) in pyridine at room temperature (27° C.) and followed by reflux at temperature 85° C. for 2.5 h. After completion of the reaction, the reaction mixture is cooled and filtered. The residue is recrystallized from water to get 5-[1-(4-nitrophenyl)-4-piperidyl]-2,3-dihydro-1,3,4-oxadiazol-2-one (5a, 1.39 g, 40%). Nitro compound (5a, 1.16 g, 4 mmol) on reduction with $SnCl_2.2H_2O$ (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5-[1-(4-aminophenyl)-4-piperidyl]-2,3-dihydro-1,3,4-oxadiazol-2-one (7a, 884 mg, 85%). To a stirred solution of 5-nitro2-furanoic acid (0.16 g, 1 mmol) in DMF add HOBT (Hydroxybenzotriazole) (0.14 g, 1 mmol), EDCI (1-Ethyl-3-(3-dimethylaminopropyl) carbodiimide)) (0.19 g, 1 mmol) and amine compound (7a, 0.26 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-4-[4-(5-oxo-4,5-dihydro-1,3,4-oxadiazol-2-yl)piperidino]phenyl-5-nitro-2-furamide (8a, 323 mg, 81%).

$^1$H NMR ($CDCl_3$, 300 MHz): 1.84-1.97 (m, 2H), 2.05-2.13 (m, 2H), 2.67-2.75 (m, 1H), 2.82-2.91 (m, 2H), 3.64-3.69 (m, 2H), 6.92 (d, 2H, J=9.06 Hz), 7.34 (d, 1H, J=3.77 Hz), 7.38 (d, 1H, J=3.77 Hz), 7.53 (d, 1H, J=9.06 Hz), 8.23 (bs, 1H); MS (ESI): m/z (400) (M+1)$^+$.

Example 2

N2-4-[4-(4-methyl-5-oxo-4,5-dihydro-1,3,4-oxadiazol-2-yl)piperidino]phenyl-5-nitro-2-furamide (8b)

5-[1-(4-Nitrophenyl)-4-piperidyl]-2,3-dihydro-1,3,4-oxadiazol-2-one (5a, 1.16 g, 4 mmol) on reacting with $CH_3I$ (0.68g, 4.8 mmol) in DMF in the presence of base $K_2CO_3$ (1.38 g, 10 mmol) at 27° C. for 10 h, after completion of the reaction, reaction mixture is poured into ice water and extracted into chloroform finally purification by column chromatography to afford pure compound 3-methyl-5-[1-(4-nitrophenyl)-4-piperidyl]-2,3-dihydro-1,3,4-oxadiazol-2-one (6a, 1.10 g, 91%). Nitro compound (6a, 1.21 g, 4 mmol) on reduction with $SnCl_2.2H_2O$ (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5-[1-(4-aminophenyl)-4-piperidyl]-3-methyl-2,3-dihydro-1,3,4-oxadiazol-2-one (7b, 960 mg, 88%). To a stirred solution of 5-nitro2-furanoic acid in DMF add HOBT (Hydroxybenzotriazole) (0.14 g, 1 mmol), EDCI (1-Ethyl-3-(3-dimethylamino propyl)carbodi imide)) (0.19 g, 1 mmol) and amine compound (7b, 0.27 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-4-[4-(4-methyl-5-oxo-4,5-dihydro-1,3,4-oxadiazol-2-yl)piperidino]phenyl-5-nitro-2-furamide (8b, 351 mg, 85%).

$^1$H NMR ($CDCl_3$, 300 MHz): δ 1.84-1.97 (m, 2H), 2.05-2.13 (m, 2H), 2.67-2.75 (m, 1H), 2.82-2.91 (m, 2H), 3.64-3.69 (m, 2H), 3.87 (s, 3H), 6.91 (d, 2H, J=9.06 Hz), 7.35 (d, 1H, J=3.77 Hz), 7.38 (d, 1H, J=3.77 Hz), 7.50 (d, 1H, J=9.06 Hz), 8.20 (bs, 1H); MS (ESI): m/z (414) (M+1)$^+$.

Example 3

N2-4-[4-(4-Ethyl-5-oxo-4,5-dihydro-1,3,4-oxadiazol-2-yl)piperidino]phenyl-5-nitro-2-furamide (8c)

5-[1-(4-Nitrophenyl)-4-piperidyl]-2,3-dihydro-1,3,4-oxadiazol-2-one (5a, 1.16 g, 4 mmol) on reacting with $C_2H_5Br$ (0.53 g, 4.8 mmol) in DMF in the presence of base $K_2CO_3$ (1.38 g, 10 mmol) at room temperature (27° C.) for 10 h, after completion of the reaction, reaction mixture is poured into ice water and extracted into chloroform finally purification by column chromatography to afford pure compound 3-ethyl-5-[1-(4-nitro phenyl)-4-piperidyl]-2,3-dihydro-1,3,4-oxadiazol-2-one (6b, 1.17 g, 92%). Nitro compound (6b, 1.27 g, 4 mmol) on reduction with $SnCl_2.2H_2O$ (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5-[1-(4-aminophenyl)-4-piperidyl]-3-ethyl-2,3-dihydro-1,3, 4-oxadiazol-2-one (7c, 1.02 g, 89%). To a stirred solution of 5-nitro2-furanoic acid in DMF add HOBT (Hydroxybenzotriazole) (0.14 g, 1 mmol), EDCI (1-Ethyl-3-(3-dimethylaminopropyl)carbodi imide)) (0.19 g, 1 mmol) and amine compound (7c, 0.29g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-4-[4-(4-ethyl-5-oxo-4,5-dihydro-1,3,4-oxadiazol-2-yl) piperi dino]phenyl-5-nitro-2-furamide (8c, 367 mg, 86%).

$^1$H NMR ($CDCl_3$, 300 MHz): δ 1.34 (t, 3H, J=7.55 Hz), 1.85-1.99 (m, 2H), 2.07-2.13 (m, 2H), 2.67-2.77 (m, 1H), 2.82-2.91 (m, 2H), 3.64-3.69 (m, 2H), 3.70-3.78 (m, 2H), 6.92 (d, 2H, J=9.06 Hz), 7.33 (d, 1H, J=3.77 Hz), 7.38 (d, 1H, J=3.77 Hz), 7.53 (d, 1H, J=9.06 Hz), 8.20 (bs, 1H); MS (ESI): m/z (450) (M+23)$^+$.

Example 4

N2-4-[4-(4-Benzyl-5-oxo-4,5-dihydro-1,3,4-oxadiazol-2-yl)piperidino]phenyl-5-nitro-2-furamide (8d)

5-[1-(4-Nitrophenyl)-4-piperidyl]-2,3-dihydro-1,3,4-oxadiazol-2-one (5a 1.16 g, 4 mmol) on reacting with $C_6H_5CH_2Br$ (0.82 g, 4.8 mmol) in DMF in the presence of base $K_2CO_3$ (1.38 g, 10 mmol) at room temperature (27° C.) for 10 h, after completion of the reaction, reaction mixture is poured into ice water and extracted into chloroform finally purification by column chromatography to afford pure compound 3-benzyl-5-[1-(4-nitrophenyl)-4-piperidyl]-2,3-dihydro-1,3,4-oxadiazol-2-one (6c, 1.42 g, 94%). Nitro compound (6c, 1.52 g, 4 mmol) on reduction with $SnCl_2.2H_2O$ (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5-[1-(4-aminophenyl)-4-piperidyl]-3-benzyl-2,3-dihydro-1,3,4-oxadiazol-2-one (7d, 1.23 g, 88%). To a stirred solution of 5-nitro2-furanoic acid in DMF add HOBT (Hydroxybenzotriazole) (0.14 g, 1 mmol), EDCI (1-Ethyl-3-(3-dimethylaminopropyl)carbodi imide)) (0.19 g, 1 mmol) and amine compound (7d, 0.35 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-4-[4-(4-benzyl-5-oxo-4,5-dihydro-1,3,4-oxadiazol-2-yl)piperidino]phenyl-5-nitro-2-furamide (8d, 405 mg, 83%).

$^1$H NMR (CDCl$_3$, 300 MHz): δ 1.83-1.97 (m, 2H), 2.05-2.11 (m, 2H), 2.65-2.75 (m, 1H), 2.82-2.91 (m, 2H), 3.62-3.69 (m, 2H), 6.91 (d, 2H, J=9.06 Hz), 7.28-7.34 (m, 5H), 7.35 (d, 1H, J=3.77 Hz), 7.38 (d, 1H, J=3.77 Hz), 7.50 (d, 1H, J=9.06 Hz), 8.19 (bs, 1H); MS (ESI): m/z (490) (M+1)$^+$.

Example 5

N2-3-Fluoro-4-[4-(5-oxo-4,5-dihydro-1,3,4-oxadiazol-2-yl)piperidino]phenyl-5-nitro-2-furamide (8e)

To a stirred solution of 3,4-difluoro nitrobenzene (1b, 3.5 g, 22 mmol) and methyl 4-piperidine carboxylate (2, 3.15 g, 22 mmol) in DMF solvent and K$_2$CO$_3$ (7.6 g, 55 mmol) as base and heated at 80° C. for 10 h, after completion of the reaction, reaction is poured into ice water and extracted into ethyl acetate finally purification by column chromatography to afford pure compound methyl 1-(2-fluoro-4-nitrophenyl)-4-piperidine carboxylate (3b, 5.33 g, 86%). To a stirred solution of ester (3b, 5.0 g, 18 mmol) in ethanol, NH$_2$NH$_2$.H$_2$O (2.25 g, 45 mmol) is added and refluxed for 12 h. After completion of the reaction ethanol is evaporated under vacuum and water is added and extracted into ethyl acetate finally purification by column chromatography to afford pure compound 1-(2-fluoro-4-nitro phenyl)-4-piperidinecarbohydrazide (4b, 4.62 g, 91%). Addition N,N-dimethyl carbamyl chloride (1.29 g, 12 mmol) to hydrazide (4b, 3.38 g, 12 mmol) in pyridine at room temperature (27° C.) and followed by reflux at temperature 85° C. for 2.5 h. After completion of the reaction, the reaction mixture is cooled and filtered. The residue is recrystallized from water to get 5-[1-(2-fluoro-4-nitrophenyl)-4-piperidyl]-2,3-dihydro-1,3,4-oxadiazol-2-one (5b, 1.47 g, 40%). Nitro compound (5b, 1.23 g, 4 mmol) on reduction with SnCl$_2$.2H$_2$O (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5-[1-(4-amino-2-fluorophenyl)-4-piperidyl]-2,3-dihydro-1,3,4-oxadiazol-2-one (7e, 920 mg, 83%). To a stirred solution of 5-nitro2-furanoic acid in DMF add HOBT (Hydroxybenzotriazole) (0.14 g, 1 mmol), EDCI (1-Ethyl-3-(3-dimethylaminopropyl)carbodi imide)) (0.19 g, 1 mmol) and amine compound (7e, 0.28 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-3-fluoro-4-[4-(5-oxo-4,5-dihydro-1,3,4-oxadiazol-2-yl)piperidino]phenyl-5-nitro-2-furamide (8e, 333 mg, 80%).

$^1$H NMR (CDCl$_3$, 300 MHz): δ 1.85-1.99 (m, 2H), 2.06-2.11 (m, 2H), 2.67-2.77 (m, 1H), 2.82-2.91 (m, 2H), 3.64-3.69 (m, 2H), 6.95 (t, 1H, J=9.06 Hz), 7.27 (dd, 1H, J=1.55, 7.55 Hz), 7.38 (d, 1H, J=3.77 Hz), 7.41 (d, 1H, J=3.77 Hz), 7.56 (dd, 1H, J=2.26, 11.25 Hz), 8.30 (bs, 1H); MS (ESI): m/z (418) (M+1)$^+$.

Example 6

N2-3-Fluoro-4-[4-(4-methyl-5-oxo-4,5-dihydro-1,3,4-oxadiazol-2-yl)piperidino]phenyl-5-nitro-2-furamide (8f)

5-[1-(2-Fluoro-4-nitrophenyl)-4-piperidyl]-2,3-dihydro-1,3,4-oxadazol-2-one (5b, 1.23 g, 4 mmol) on reacting with CH$_3$I (0.68 g, 4.8 mmol) in DMF in the presence of base K$_2$CO$_3$ (1.38 g, 10 mmol) at 0° C. for 10 h, after completion of the reaction, reaction mixture is poured into ice water and extracted into chloroform finally purification by column chromatography to afford pure compound 5-[1-(2-fluoro-4-nitrophenyl)-4-piperidyl]-3-methyl-2,3-dihydro-1,3,4-oxadiazol-2-one (6d, 1.18 g, 92%). Nitro compound (6d, 1.29 g, 4 mmol) on reduction with SnCl$_2$.2H$_2$O (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5[1-(4-amino-2-fluorophenyl)-4-piperidyl]-3-methyl-2,3-dihydro-1,3,4-oxadiazol-2-one (7f, 920 mg, 83%). To a stirred solution of 5-nitro2-furanoic acid in DMF add HOBT (Hydroxybenzotriazole) (0.14 g, 1 mmol), EDCI (1-Ethyl-3-(3-dimethylaminopropyl)carbodi imide)) (0.19 g, 1 mmol) and amine compound (7f, 0.29 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-3-fluoro-4-[4-(4-methyl-5-oxo-4,5-dihydro-1,3,4-oxadiazol-2-yl)piperidino]phenyl-5-nitro-2-furamide (8f, 375 mg, 87%).

$^1$H NMR (CDCl$_3$, 300 MHz): δ 1.84-1.97 (m, 2H), 2.05-2.13 (m, 2H), 2.67-2.75 (m, 1H), 2.82-2.91 (m, 2H), 3.64-3.69 (m, 2H), 3.87 (s, 3H), 6.94 (t, 1H, J=9.06 Hz), 7.27 (dd, 1H, J=1.51, 7.55 Hz), 7.38 (d, 1H, J=3.77 Hz), 7.44 (d, 1H, J=3.77 Hz), 7.58 (dd, 1H, J=2.25, 13.59 Hz), 8.33 (bs, 1H); MS (ESI): m/z (454) (M+23)$^+$.

Example 7

N2-4-[4-(4-Ethyl-5-oxo-4,5-dihydro-1,3,4-oxadiazol-2-yl)piperi-dino]-3-fluoro phenyl-5-nitro-2-furamide (8g)

5-[1-(2-Fluoro-4-nitrophenyl)-4-piperidyl]-2,3-dihydro-1,3,4-oxadiazol-2-one (5b, 1.23 g, 4 mmol) on reacting with C$_2$H$_5$Br (0.53 g, 4.8 mmol) in DMF in the presence of base K$_2$CO$_3$ (1.38 g, 10 mmol) at room temperature (27° C.) for 10 h, after completion of the reaction, reaction mixture is poured into ice water and extracted into chloroform finally purification by column chromatography to afford pure compound 3-ethyl-5-[1-(2-fluoro-4-nitrophenyl)-4-piperidyl]-2,3-dihydro-1,3,4-oxadiazol-2-one (6e, 1.27 g, 95%). Nitro compound (6e, 1.34 g, 4 mmol) on reduction with SnCl$_2$.2H$_2$O (2.71 g, 12 mmol) in methanol and refluxed at 65° C. for 4 h, after completion of reaction methanol is evaporated under vacuum and to this saturated sodium bicarbonate solution, is added to quench the excess stannous chloride and filtered through celite bed and purified in silica column (60-120) to afforded pure compound 5-[1-(4-amino-2-fluorophenyl)-4-piperidyl]-3-ethyl-2,3-dihydro-1,3,4-oxadiazol-2-one (7 g, 1.05 g, 86%). To a stirred solution of 5-nitro2-furanoic acid in DMF add HOBT (Hydroxybenzo triazole) (0.14 g, 1 mmol), EDCI (1-Ethyl-3-(3-dimethylaminopropyl)carbodi imide))

(0.19 g, 1 mmol) and amine compound (7g, 0.3 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-4-[4-(4-ethyl-5-oxo-4,5-dihydro-1,3,4-oxadiazol-2-yl)piperidino]-3-fluorophenyl-5-nitro-2-furamide (8 g, 391 mg, 88%).

$^1$H NMR (CDCl$_3$, 300 MHz): δ 1.34 (t, 3H, J=7.55 Hz), 1.96-2.05 (m, 2H), 2.06-2.14 (m, 2H), 2.68-2.75 (m, 1H), 2.77-2.86 (m, 2H), 3.43-3.50 (m, 2H), 3.72-3.79 (m, 2H), 6.96 (t, 1H, J=9.06 Hz), 7.28 (dd, 1H, J=1.51, 7.55 Hz), 7.37 (d, 1H, J=3.77 Hz), 7.42 (d, 1H, J=3.77 Hz), 7.58 (dd, 1H, J=2.26, 13.59 Hz), 8.32 (bs, 1H); MS (ESI): m/z (446) (M+1)$^+$.

Example 8

N2-4-[4-(4-Benzyl-5-oxo-4,5-dihydro-1,3,4-oxadiazol-2-yl)piperi dino]-3-fluoro phen yl-5-nitro-2-furamide (8h)

5-[1-(2-Fluoro-4-nitrophenyl)-4-piperidyl]-2,3-dihydro-1,3,4-oxadiazol-2-one (5b, 1.23 g, 4 mmol) on reacting with C$_6$H$_5$CH$_2$Br (0.82 g, 1 mmol) in DMF in the presence of base K$_2$CO$_3$ (1.38 g, 10 mmol) at room temperature (27° C.) for 10 h, after completion of the reaction, reaction mixture is poured into ice water and extracted into chloroform finally purification by column chromatography to afford pure compound 3-benzyl-5-[1-(2-fluoro-4-nitrophenyl)-4-piperidyl]-2,3-dihydro-1,3,4-oxadiazol-2-one (6f, 1.52 g, 96%). Nitro compound (6f, 1.59 g, 4 mmol) on reduction with SnCl$_2$.2H$_2$O (2.71 g, 12 mmol) in methanol and refluxed at 65° C. for 4 h, after completion of reaction methanol is evaporated under vacuum and to this saturated sodium bicarbonate solution is added to quench the excess stannous chloride and filtered through celite bed and purified in silica column (60-120) to afforded pure compound 5-[1-(4-amino-2-fluorophenyl)-4-piperidyl]-3-benzyl-2,3-dihydro-1,3,4-oxadiazol-2-one (7 h, 1.26 g, 86%). To a stirred solution of 5-nitro2-furanoic acid in DMF add. HOBT (Hydroxybenzotriazole) (0.14 g, 1 mmol), EDCI (1-Ethyl-3-(3-dimethyl aminopropyl)carbodi imide)) (0.19 g, 1 mmol) and amine compound (7 h, 0.36 g, 1 mmol) and stirred for 2 h at room temperature (27° C.), after completion of the reaction, reaction mixture is poured into ice water and extracted into chloroform finally purification by column chromatography using ethyl acetate-hexane (7:3) as eluant to afford pure compound N2-4-[4-(4-benzyl-5-oxo-4,5-dihydro-1,3,4-oxadiazol-2-yl)piperi dino]-3-fluorophenyl-5-nitro-2-furamide (8 h, 430 mg, 85%).

$^1$H NMR (CDCl$_3$, 300 MHz): δ 1.89-2.00 (m, 2H), 2.02-2.11 (m, 2H), 2.65-2.72 (m, 1H), 2.73-2.82 (m, 2H), 3.42-3.46 (m, 2H), 4.83 (s, 2H), 6.92 (t, 1H, J=9.06 Hz), 7.25 (d, 2H, J=7.55 Hz), 7.30-7.39 (m, 5H), 7.39 (d, 1H, J=3.77 Hz), 7.55 (dd, 1H, J=2.26, 13.59 Hz); MS (ESI): m/z (508) (M+1)$^+$.

Example 9

5-[1-(4-[(E)-1-(5-Nitro-2-furyl)methylidene]aminophenyl)-4-piperidyl]-2,3-dihydro-1,3,4-oxadiazol-2-one (9a)

5-[1-(4-Aminophenyl)-4-piperidyl]-2,3-dihydro-1,3,4-oxadiazol-2-one (7a, 0.26 g, 1 mmol) on reacting with 5-nitro2-furaldehyde in the presence of catalytic amount of CH$_3$COOH (3 drops) in methanol at 0° C. for 10 h and the obtained solid is filtered, washed with water and recrystallized in ethanol to obtain product 5-[1-(4-[(E)-1-(5-nitro-2-furyl)methylidene]aminophenyl)-4-piperidyl]-2,3-dihydro-1,3,4-oxadiazol-2-one (9a, 306 mg, 80%).

$^1$H NMR (CDCl$_3$, 300 MHz): δ 1.84-1.96 (m, 2H), 2.06-2.12 (m, 2H), 2.70-2.80 (m, 1H), 2.91-2.99 (m, 2H), 3.71-3.77 (m, 2H), 6.92 (d, 2H, J=9.06 Hz), 7.14 (d, 1H, J=4.53 Hz), 7.23-7.31 (m, 2H), 7.39 (d, 1H, J=4.53 Hz), 8.20 (s, 1H); 8.36 (bs, 1H); MS (ESI): m/z (384) (M+1)$^+$.

Example 10

3-Methyl-5-[1-(4-[(E)-1-(5-nitro-2-furyl)methylidene]aminophenyl)-4-piperidyl]-2,3-dihydro-1,3,4-oxadiazol-2-one (9b)

5-[1-(4-Aminophenyl)-4-piperidyl]-3-methyl-2,3-dihydro-1,3,4-oxadiazol-2-one (7b, 0.27 g, 1 mmol) on reacting with 5-nitro2-furaldehyde in the presence of catalytic amount of CH$_3$COOH (3 drops) in methanol at 0° C. for 10 h and the obtained solid is filtered, washed with water and recrystallized in ethanol to obtain product 3-methyl-5-[1-(4-[(E)-1-(5-nitro-2-furyl)methylidene]aminophenyl)-4-piperidyl]-2,3-dihydro-1,3,4-oxadiazol-2-one (9b, 341 mg, 86%).

$^1$H NMR (CDCl$_3$, 300 MHz): δ 1.84-1.97 (m, 2H), 2.07-2.13 (m, 2H), 2.70-2.81 (m, 1H), 2.91-3.00 (m, 2H), 3.39 (s, 3H), 3.71-3.78 (m, 2H), 6.93 (d, 2H, J=9.06 Hz), 7.13 (d, 1H, J=4.53 Hz), 7.25-7.32 (m, 2H), 7.39 (d, 1H, J=3.77 Hz), 8.41 (s, 1H); MS (ESI): m/z (420) (M+23)$^+$.

Example 11

3-Ethyl-5-[1-(4-[(E)-1-(5-nitro-2-furyl)methylidene]aminophenyl)-4-piperidyl]-2,3-dihydro-1,3,4-oxadiazol-2-one (9c)

5-[1-(4-Aminophenyl)-4-piperidyl]-3-ethyl-2,3-dihydro-1,3,4-oxadiazol-2-one (7c, 0.29 g, 1 mmol) on reacting with 5-nitro2-furaldehyde in the presence of catalytic amount of CH$_3$COOH (3 drops) in methanol at 0° C. for 10 h and the obtained solid is filtered, washed with water and recrystallized in ethanol to obtain product 3-ethyl-5-[1-(4-[(E)-1-(5-nitro-2-furyl)methylidene]aminophenyl)-4-piperidyl]-2,3-dihydro-1,3,4-oxadiazol-2-one (9c, 357 mg, 87%).

$^1$H NMR (CDCl$_3$, 300 MHz): δ 1.35 (t, 3H, J=7.55 Hz), 1.87-1.99 (m, 2H), 2.07-2.12 (m, 2H), 2.67-2.76 (m, 1H), 2.82-2.91 (m, 2H), 3.66-3.69 (m, 2H), 3.69-3.77 (m, 2H), 6.92 (d, 2H, J=9.06 Hz), 7.15 (d, 1H, J=3.77 Hz), 7.26-7.31 (m, 2H), 7.40 (d, 1H, J=3.77 Hz), 8.40 (s, 1H); MS (ESI): m/z (434) (M+23)$^+$.

Example 12

3-Benzyl-5-[1-(4-[(E)-1-(5-nitro-2-furyl)methylidene]aminophenyl)-4-piperidyl]-2,3-dihydro-1,3,4-oxadiazol-2-one (9d)

5-[1-(4-Aminophenyl)-4-piperidyl]-3-benzyl-2,3-dihydro-1,3,4-oxadiazol-2-one (7d, 0.35 g, 1 mmol) on reacting with 5-nitro-2-furaldehyde in the presence of catalytic amount of CH$_3$COOH (3 drops) in methanol at 0° C. for 10 h and the obtained solid is filtered, washed with water and recrystallized in ethanol to obtain product 3-benzyl-5-[1-(4-[(E)-1-(5-nitro-2-furyl)methylidene]aminophenyl)-4-piperidyl]-2,3-dihydro-1,3,4-oxadiazol-2-one (9d, 416 mg, 88%).

$^1$H NMR (CDCl$_3$, 300 MHz): δ 1.85-1.99 (m, 2H), 2.07-2.13 (m, 2H), 2.67-2.77 (m, 1H), 2.82-2.90 (m, 2H), 3.63-

3.69 (m, 2H), 3.70-3.78 (m, 2H), 4.81 (s, 2H), 6.92 (d, 2H, J=9.06 Hz), 7.17 (d, 1H, J=3.77 Hz), 7.25-7.30 (m, 2H), 7.32-7.37 (m, 5H), 7.38 (d, 1H, J=3.77 Hz), 8.41 (s, 1H); MS (ESI): m/z (474) (M+1)$^+$.

Example 13

5-[1-(2-Fluoro-4-[(E)-1-(5-nitro-2-furyl)methylidene]aminophenyl)-4-piperidyl]-2,3-dihydro-1,3,4-oxadiazol-2-one (9e)

5-[1-(4-Amino-2-fluorophenyl)-4-piperidyl]-2,3-dihydro-1,3,4-oxadiazol-2-one (7e, 0.28 g, 1 mml) on reacting with 5-nitro2-furaldehyde in the presence of catalytic amount of $CH_3COOH$ (3 drops) in methanol at 0° C. for 10 h and the obtained solid is filtered, washed with water and recrystallized in ethanol to obtain product 5-[1-(2-fluoro-4-[(E)-1-(5-nitro-2-furyl)methylidene]aminophenyl)-4-piperidyl]-2,3-dihydro-1,3,4-oxadiazol-2-one (9e, 324 mg, 81%).

$^1$H NMR (CDCl$_3$, 300 MHz): δ 1.97-2.04 (m, 2H), 2.11-2.14 (m, 2H), 2.73-2.81 (m, 1H), 2.86-2.91 (m, 2H), 3.53-3.55 (m, 2H), 6.97 (t, 1H, J=7.84 Hz), 7.09 (t, 2H, J=7.84 Hz), 7.16 (d, 1H, J=2.94 Hz), 7.41 (d, 1H, J=2.94 Hz), 8.37 (s, 1H), 8.73 (bs, 1H); MS (ESI): m/z (402) (M+1)$^+$.

Example 14

5-[1-(2-Fluoro-4-[(E)-1-(5-nitro-2-furyl)methylidene]aminophenyl)-4-piperidyl]-3-methyl-2,3-dihydro-1,3,4-oxadiazol-2-one (9f)

5-[1-(4-Amino-2-fluorophenyl)-4-piperidyl]-3-methyl-2,3-dihydro-1,3,4-oxadiazol-2-one (7f, 0.29 g, 1 mmol) on reacting with 5-nitro2-furaldehyde in the presence of catalytic amount of $CH_3COOH$ (3 drops) in methanol at 0° C. for 10 h and the obtained solid is filtered, washed with water and recrystallized in ethanol to obtain product 5-[1-(2-fluoro-4-[(E)-1-(5-nitro-2-furyl)methylidene]aminophenyl)-4-piperidyl]-3-methyl-2,3-dihydro-1,3,4-oxadiazol-2-one (9f, 352 mg, 85%).

$^1$H NMR (CDCl$_3$, 300 MHz): δ 1.92-2.01 (m, 2H), 2.03-2.14 (m, 2H), 2.69-2.77 (m, 1H), 2.83-2.91 (m, 2H), 3.40 (s, 3H), 3.50-3.57 (m, 2H), 6.95 (t, 1H, J=9.06 Hz), 7.03-7.09 (m, 2H), 7.16 (d, 1H, J=3.77 Hz), 7.40 (d, 1H, J=3.77 Hz), 8.37 (s, 1H); MS (ESI): m/z (416) (M+1)$^+$.

Example 15

3-Ethyl-5-[1-(2-fluoro-4-[(E)-1-(5-nitro-2-furyl)methylidene]aminophenyl)-4-piperidyl]-2,3-dihydro-1,3,4-oxadiazol-2-one (9g)

5-[1-(4-Amino-2-fluorophenyl)-4-piperidyl]-3-ethyl-2,3-dihydro-1,3,4-oxadiazol-2-one (7 g, 0.30 g, 1 mmol) on reacting with 5-nitro2-furaldehyde in the presence of catalytic amount of $CH_3COOH$ (3 drops) in methanol at 0° C. for 10 h and the obtained solid is filtered, washed with water and re-crystallized in ethanol to obtain product 3-ethyl-5-[1-(2-fluoro-4-[(E)-1-(5-nitro-2-furyl)methylidene]aminophenyl)-4-piperidyl]-2,3-dihydro-1,3,4-oxadiazol-2-one (9 g, 373 mg, 87%).

$^1$H NMR (CDCl$_3$, 300 MHz): δ 1.34 (t, 3H, J=7.55 Hz), 1.89-1.99 (m, 2H), 2.05-2.13 (m, 2H), 2.69-2.77 (m, 1H), 2.82-2.91 (m, 2H), 3.59-3.66 (m, 2H), 3.70-3.78 (m, 2H), 6.92 (t, 1H, J=9.06 Hz), 7.05-7.10 (m, 2H), 7.17 (d, 1H, J=3.77 Hz), 7.43 (d, 1H, J=3.77 Hz), 8.36 (s, 1H); MS (ESI): m/z (430) (M+1)$^+$.

Example 16

3-Benzyl-5-[1-(2-fluoro-4-[(E)-1-(5-nitro-2-furyl)methylidene]aminophenyl)-4-piperidyl]-2,3-dihydro-1,3,4-oxadiazol-2-one (9 h)

5-[1-(4-Amino-2-fluorophenyl)-4-piperidyl]-3-benzyl-2,3-dihydro-1,3,4-oxadiazol-2-one (7 h, 0.36 g, 1 mmol) on reacting with 5-nitro2-furaldehyde in the presence of catalytic amount of $CH_3COOH$ (3 drops) in methanol at 0° C. for 10 h and the obtained solid is filtered, washed with water and recrystallized in ethanol to obtain product 3-benzyl-5-[1-(2-fluoro-4-[(E)-1-(5-nitro-2-furyl)methylidene]amino phenyl)-4-piperidyl]-2,3-dihydro-1,3,4-oxadiazol-2-one (9 h, 432 mg, 88%).

$^1$H NMR (CDCl$_3$, 300 MHz): δ 1.91-2.00 (m, 2H), 2.02-2.12 (m, 2H), 2.67-2.77 (m, 1H), 2.80-2.88 (m, 2H), 3.48-3.54 (m, 2H), 4.82 (s, 2H), 6.93 (t, 1H, J=9.06 Hz), 7.02-7.09 (m, 2H), 7.15 (d, 1H, J=3.77 Hz), 7.32-7.36 (m, 5H), 7.39 (d, 1H, J=3.77 Hz), 8.36 (s, 1H); MS (ESI): m/z (492) (M+1)$^+$.

Example 17

5-[1-(4[(5-Nitro-2-furyl)methyl]aminophenyl)-4-piperidyl]-2,3-dihydro-1,3,4-oxadiazol-2-one (10a)

5-[1-(4-[(E)-1-(5-Nitro-2-furyl)methylidene]aminophenyl)-4-piperidyl]-2,3-dihydro-1,3,4-oxadiazol-2-one (9a, 0.38 g, 1 mmol) on reduction with sodiumcyano borohydride (0.12 g, 2 mmol) in the presence of catalytic amount of $CH_3COOH$ (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 5-[1-(4-[(5-nitro-2-furyl)methyl]aminophenyl)-4-piperidyl]-2,3-dihydro-1,3,4-oxadiazol-2-one (10a, 315 mg, 82%).

$^1$H NMR (CDCl$_3$, 300 MHz): δ 1.85-1.94 (m, 2H), 2.00-2.09 (m, 2H), 2.60-2.67 (m, 1H), 2.76-2.83 (m, 2H), 3.24-3.29 (m, 2H), 4.35 (s, 2H), 5.33 (bs, 1H), 6.42 (d, 1H, J=2.89 Hz), 6.55 (d, 2H, J=8.68 Hz), 6.82 (d, 2H, J=8.68 Hz), 7.21 (d, 1H, J=3.84 Hz), 7.50 (bs, 1H); MS (ESI): m/z (386) (M+1)$^+$.

Example 18

3-Methyl-5-[1-(4-[(5-nitro-2-furyl)methyl]aminophenyl)-4-piperidyl]-2,3-dihydro-1,3,4-oxadiazol-2-one (10b)

3-Methyl-5-[1-(4-[(E)-1-(5-nitro-2-furyl)methylidene]aminophenyl)-4-piperidyl]-2,3-dihydro-1,3,4-oxadiazol-2-one (9b, 0.40 g, 1 mmol) on reduction with sodiumcyanoborohydride (0.12 g, 2 mmol) in the presence of catalytic amount of $CH_3COOH$ (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 3-methyl-5-[1-(4-[(5-nitro-2-furyl)methyl]aminophenyl)-4-piperidyl]-2,3-dihydro-1,3,4-oxadiazol-2-one (10b, 343 mg, 86%).

$^1$H NMR (CDCl$_3$, 300 MHz): δ 1.87-1.95 (m, 2H), 2.02-2.10 (m, 2H), 2.60-2.68 (m, 1H), 2.70-2.75 (m, 2H), 3.38 (s, 3H), 3.43-3.49 (m, 2H), 4.39 (s, 2H), 6.41 (d, 1H, J=2.89 Hz), 6.56 (d, 2H, J=8.68 Hz), 6.81 (d, 2H, J=8.68 Hz), 7.20 (d, 1H, J=3.86 Hz), 7.25 (s, 1H); MS (ESI): m/z (400) (M+1)$^+$.

Example 19

3-Ethyl-5-[1-(4-[(5-nitro-2-furyl)methyl]aminophenyl)-4-piperidyl]-2,3-dihydro-1,3,4-oxadiazol-2-one (10c)

3-Ethyl-5-[1-(4[(E)-1-(5-nitro-2-furyl)methylidene]aminophenyl)-4-piperidyl]-2,3-dihydro-1,3,4-oxadiazol-2-one (9c, 0.41 g, 1 mmol) on reduction with sodiumcyano borohydride (0.12 g, 2 mmol) in the presence of catalytic amount of CH$_3$COOH (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 3-ethyl-5-[1-(4-[(5-nitro-2-furyl)methyl]aminophenyl)-4-piperidyl]-2,3-dihydro-1,3,4-oxadiazol-2-one (10c, 359 mg, 87%).

$^1$H NMR (CDCl$_3$, 300 MHz): δ 1.34 (t, 3H, J=7.17 Hz), 1.86-1.99 (m, 2H), 2.04-2.11 (m, 2H), 2.61-2.67 (m, 1H), 2.70-2.78 (m, 2H), 3.44-3.50 (m, 2H), 3.70-3.77 (m, 2H), 4.40 (s, 2H), 6.43 (d, 1H, J=3.58 Hz), 6.57 (d, 2H, J=8.87 Hz), 6.83 (d, 2H, J=8.87 Hz), 7.23 (d, 1H, J=3.58 Hz), 7.26 (s, 1H); MS (ESI): m/z (414) (M+1)$^+$.

Example 20

3-Benzyl-5-[1-(4-[(5-nitro-2-furyl)methyl]aminophenyl)-4-piperidyl]-2,3-dihydro-1,3,4-oxadiazol-2-one (10d)

3-Benzyl-5-[1-(4-[(E)-1-(5-nitro-2-furyl)methylidene]aminophenyl)-4-piperidyl]-2,3-dihydro-1,3,4-oxadiazol-2-one (9d, 0.47 g, 1 mmol) on reduction with sodiumcyano borohydride (0.12 g, 2 mmol) in the presence of catalytic amount of CH$_3$COOH (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 3-benzyl-5-[1-(4-[(5-nitro-2-furyl) methyl]aminophenyl)-4-piperidyl]-2,3-dihydro-1,3,4-oxadiazol-2-one (10d, 403 mg, 85%).

$^1$H NMR (CDCl$_3$, 300 MHz): δ 1.82-1.95 (m, 2H), 2.05-2.11 (m, 2H), 2.68-2.76 (m, 1H), 2.77-2.90 (m, 2H), 3.62-3.67 (m, 2H), 4.82 (s, 2H), 6.88 (d, 2H, J=9.06 Hz), 7.30-7.36 (m, 51-1), 7.39 (d, 1H, J=3.77 Hz), 7.44 (d, 1H, J=3.77 Hz), 7.63 (d, 2H, J=9.06 Hz), 10.00 (bs, 1H); MS (ESI): m/z (498) (M+23)$^+$.

Example 21

5-[1-(2-Fluoro-4-[(5-nitro-2-furyl)methyl]aminophenyl)-4-piperidyl]-2,3-dihydro-1,3,4-oxadiazol-2-one (10e)

5-[1-(2-Fluoro-4-[(E)-1-(5-nitro-2-furyl)methylidene]aminophenyl)-4-piperidyl]-2,3-dihydro-1,3,4-oxadiazol-2-one (9e, 0.40 g, 1 mmol) on reduction with sodiumcyano borohydride (0.12 g, 2 mmol) in the presence of catalytic amount of CH$_3$COOH (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 5-[1-(2-fluoro-4-[(5-nitro-2-furyl)methyl]aminophenyl)-4-piperidyl]-2,3-dihydro-1,3,4-oxadiazol-2-one (10e, 326 mg, 81%).

$^1$H NMR (CDCl$_3$, 300 MHz): δ 1.86-1.95 (m, 2H), 1.98-2.08 (m, 2H), 2.58-2.64 (m, 1H), 2.66-2.74 (m, 2H), 3.24-3.28 (m, 2H), 4.36 (s, 2H), 5.32 (bs, 1H), 6.32-6.42 (m, 2H), 6.52 (d, 1H, J=3.58 Hz), 6.81 (t, 1H, J=9.06 Hz), 7.28 (d, 1H, J=3.58 Hz), 7.50 (bs, 1H); MS (ESI): m/z (404) (M+1)$^+$.

Example 22

5-[1-(2-Fluoro-4-[(5-nitro-2-furyl)methyl]aminophenyl)-4-piperidyl]-3-methyl-2,3-dihydro-1,3,4-oxadiazol-2-one (10f)

5-[1-(2-Fluoro-4-[(E)-1-(5-nitro-2-furyl)methylidene]aminophenyl)-4-piperidyl]-3-methyl-2,3-dihydro-1,3,4-oxadiazol-2-one (9f, 0.42 g, 1 mmol) on reduction with sodium cyanoboro hydride (0.12 g, 2 mmol) in the presence of catalytic amount of CH$_3$COOH (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 5-[1-(2-fluoro-4-[(5-nitro-2-furyl)methyl]aminophenyl)-4-piperidyl]-3-methyl-2,3-dihydro-1,3,4-oxadiazol-2-one (10f, 358 mg, 86%).

$^1$H NMR (CDCl$_3$, 300 MHz): δ 1.92-2.00 (m, 2H), 2.01-2.08 (m, 2H), 2.60-2.66 (m, 1H), 2.67-2.77 (m, 2H), 3.25-3.32 (m, 2H), 3.38 (s, 3H), 4.38 (s, 2H), 6.29-6.38 (m, 2H), 6.43 (d, 1H, J=3.77 Hz), 6.80 (t, 1H, J=9.06 Hz), 7.21 (d, 1H, J=3.77 Hz); MS (ESI): m/z (418) (M+1)$^+$.

Example 23

3-Ethyl-5-[1-(2-fluoro-4-[(5-nitro-2-furyl)methyl]aminophenyl)-4-piperidyl]-2,3-di hydro-1,3,4-oxadiazol-2-one (10g)

3-Ethyl-5-[1-(2-fluoro-4-[(E)-1-(5-nitro-2-furyl)methylidene]aminophenyl)-4-piperidyl]-2,3-dihydro-1,3,4-oxadiazol-2-one (9 g, 0.43 g, 1 mmol) on reduction with sodiumcyanoborohydride (0.12 g, 2 mmol) in the presence of catalytic amount of CH$_3$COOH (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 3-ethyl-5-[1-(2-fluoro-4-[(5-nitro-2-furyl)methyl]aminophenyl)-4-piperidyl]-2,3-dihydro-1,3,4-oxadi azol-2-one (10g, 357 mg, 83%).

$^1$H NMR (CDCl$_3$, 300 MHz): δ 1.35 (t, 3H, J=8.65 Hz), 1.90-2.00 (m, 2H), 2.00-2.09 (m, 2H), 2.60-2.65 (m, 1H), 2.67-2.77 (m, 2H), 3.26-3.31 (m, 2H), 3.71-3.75 (m, 2H), 4.37 (s, 2H), 6.29-6.38 (m, 2H), 6.42 (d, 1H, J=3.77 Hz), 6.81 (t, 1H, J=9.06 Hz), 7.21 (d, 1H, J=3.77 Hz); MS (ESI): m/z (432) (M+1)$^+$.

Example 24

3-Benzyl-5-[1-(2-fluoro-4-[(5-nitro-2-furyl)methyl] aminophenyl)-4-piperidyl]-2,3-di hydro-1,3,4-oxadiazol-2-one (10 h)

3-Benzyl-5-[1-(2-fluoro-4-[(E)-1-(5-nitro-2-furyl)methylidene]aminophenyl)-4-piperidyl]-2,3-dihydro-1,3,4-oxadiazol-2-one (9 h, 0.49 g, 1 mmol) on reduction with sodiumcyanoborohydride (0.12 g, 2 mmol) in the presence of catalytic amount of $CH_3COOH$ (3 drops) in methanol at 0° C. for 12 h. After completion of the reaction as indicated by TLC, the reaction mixture is neutralized with sodium bi carbonate and extracted into chloroform. The crude product thus obtained was purified by column chromatography using ethyl acetate-hexane (8:2) as eluant to obtain product 3-benzyl-5-[1-(2-fluoro-4-[(5-nitro-2-furyl)methyl]aminophenyl]-4-piperidyl]-2,3-dihydro-1,3,4-oxadiazol-2-one (10 h, 414 mg, 84%).

$^1$H NMR (CDCl$_3$, 300 MHz): δ 1.86-1.96 (m, 2H), 1.98-2.06 (m, 2H), 2.58-2.64 (m, 1H), 2.65-2.73 (m, 2H), 3.23-3.30 (m, 2H), 4.37 (s, 2H), 4.81 (s, 2H), 6.29-6.38 (m, 2H), 6.43 (d, 1H, J=3.77 Hz), 6.80 (t, 1H, J=9.06 Hz), 7.22 (d, 1H, J=3.77 Hz), 7.31-7.34 (m, 5H); MS (ESI): m/z (494) (M+1)$^+$.

Example 25

5-(1-(4-(1-((5-Nitro-2-furyl)methyl)ammonio)phenyl)-4-piperidyl)-2,3-dihydro-1,3,4-oxadiazol-2-one chloride 5-[1-(4-[(5-Nitro-2-furyl)methyl]aminophenyl)-4-piperidyl]-2,3-dihydro-1,3,4-oxadiazol-2-one (10a, 192 mg, 0.5 mmol) was taken in 5 mL of 1 N methanolic HCl and stirred for 1 h at 0° C. Methanol was removed under reduced pressure to get 5-(1-(4-(1-((5-nitro-2-furyl)methyl)ammonio)phenyl)-4-piperidyl)-2,3-dihydro-1,3,4-oxadiazol-2-one chloride as brown solid.

Example 26

3-Methyl-5-(1-(4-(1-((5-nitro-2-furyl)methyl)ammonio)phenyl)-4-piperidyl)-2,3-dihydro-1,3,4-oxadiazol-2-one chloride 3-Methyl-5-[1-(4-[(5-nitro-2-furyl)methyl]aminophenyl)-4-piperidyl]-2,3-dihydro-1,3,4-oxadiazol-2-one (10b, 200 mg, 0.5 mmol) was taken in 5 mL of 1 N methanolic HCl and stirred for 1 h at 0° C. Methanol was removed under reduced pressure to get 3-methyl-5-(1-(4-(1-((5-nitro-2-furyl)methyl)ammonio)phenyl)-4-piperidyl)-2,3-dihydro-1,3,4-oxadiazol-2-one chloride as brown solid.

Example 27

3-Ethyl-5-(1-(4-(1-((5-nitro-2-furyl)methyl)ammonio)phenyl)-4-piperidyl)-2,3-dihydro-1,3,4-oxadiazol-2-one chloride 3-Ethyl-5-[1-(4-[(5-nitro-2-furyl)methyl]aminophenyl)-4-piperidyl]-2,3-dihydro-1,3,4-oxadiazol-2-one (10c, 206 mg, 0.5 mmol) was taken in 5 mL of 1 N methanolic HCl and stirred for 1 h at 0° C. Methanol was removed under reduced pressure to get 3-ethyl-5-(1-(4-(1-((5-nitro-2-furyl)methyl)ammonio)phenyl)-4-piperidyl)-2,3-dihydro-1,3,4-oxadiazol-2-one chloride as brown solid.

Example 28

3-Benzyl-5-(1-(4-(1-((5-nitro-2-furyl)methyl)ammonio)phenyl)-4-piperidyl)-2,3-dihydro-1,3,4-oxadiazol-2-one chloride 3-Benzyl-5-[1-(4-[(5-nitro-2-furyl)methyl]aminophenyl)-4-piperidyl]-2,3-dihydro-1,3,4-oxadiazol-2-one (10d, 235 mg, 0.5 mmol) was taken in 5 mL of 1 N methanolic HCl and stirred for 1 h at 0° C. Methanol was removed under reduced pressure to get 3-benzyl-5-(1-(4-(1-((5-nitro-2-furyl)methyl)ammonio)phenyl)-4-piperidyl)-2,3-dihydro-1,3,4-oxadiazol-2-one chloride as brown solid.

Example 29

5-(1-(2-Fluoro-4-(1-((5-nitro-2-furyl)methyl)ammonio)phenyl)-4-piperidyl)-2,3-dihydro-1,3,4-oxadiazol-2-one chloride 5-[1-(2-Fluoro-4-[(5-nitro-2-furyl)methyl]aminophenyl)-4-piperidyl]-2,3-dihydro-1,3,4-oxadiazol-2-one (10e, 201 mg, 0.5 mmol) was taken in 5 mL of 1 N methanolic HCl and stirred for 1 h at 0° C. Methanol was removed under reduced pressure to get 5-(1-(2-fluoro-4-(1-((5-nitro-2-furyl)methyl)ammonio)phenyl)-4-piperidyl)-2,3-dihydro-1,3,4-oxadiazol-2-one chloride as brown solid.

Example 30

5-(1-(2-Fluoro-4-(1-((5-nitro-2-furyl)methyl)ammonio)phenyl)-4-piperidyl)-3-methyl-2,3-dihydro-1,3,4-oxadiazol-2-one chloride 5-[1-(2-Fluoro-4-[(5-nitro-2-furyl)methyl]aminophenyl)-4-piperidyl]-3-methyl-2,3-dihydro-1,3,4-oxadiazol-2-one (10f, 208 mg, 0.5 mmol) was taken in 5 mL of 1 N methanolic HCl and stirred for 1 h at 0° C. Methanol was removed under reduced pressure to get 5-(1-(2-fluoro-4-(1-((5-nitro-2-furyl)methyl)ammonio)phenyl)-4-piperidyl)-3-methyl-2,3-dihydro-1,3,4-oxadiazol-2-one chloride as brown solid.

Example 31

3-Ethyl-5-(1-(2-fluoro-4-(1-((5-nitro-2-furyl)methyl)ammonio)phenyl)-4-piperidyl)-2,3-dihydro-1,3,4-oxadiazol-2-one chloride 3-Ethyl-5-[1-(2-fluoro-4-[(5-nitro-2-furyl)methyl]aminophenyl)-4-piperidyl]-2,3-di hydro-1,3,4-oxadiazol-2-one (10g, 215 mg, 0.5 mmol) was taken in 5 mL of 1 N methanolic HCl and stirred for 1 h at 0° C. Methanol was removed under reduced pressure to get 3-ethyl-5-(1-(2-fluoro-4-(1-((5-nitro-2-furyl)methyl)ammonio)phenyl)-4-piperidyl)-2,3-dihydro-1,3,4-oxadiazol-2-one chloride as brown solid.

Example 32

3-Benzyl-5-(1-(2-fluoro-4-(1-((5-nitro-2-furyl)methyl)ammonio)phenyl)-4-piperidyl)-2,3-dihydro-1,3,4-oxadiazol-2-one chloride 3-Benzyl-5-[1-(2-fluoro-4-[(5-nitro-2-furyl)methyl]aminophenyl)-4-piperidyl]-2,3-di hydro-1,3,4-oxadiazol-2-one (10 h, 247 mg, 0.5 mmol) was taken in 5 mL of 1 N methanolic HCl and stirred for 1 h at 0° C. Methanol was removed under reduced pressure to get 3-benzyl-5-(1-(2-fluoro-4-(1-((5-nitro-2-furyl)methyl)ammonio)phenyl)-4-piperidyl)-2,3-dihydro-1,3,4-oxadiazol-2-one chloride as brown solid.

BIOLOGICAL ACTIVITY

Antimycobacterial Assay

The anti-mycobacterial activities of novel nitrofurfuryl substituted phenyl linked piperidino-oxadiazolone congeners (8a-h, 9a-h and 10a-h) have been evaluated for the antimycobacterial activity and the results are summarized in Table 1. All compounds were initially screened against *M. tuberculosis* H$_{37}$Rv at the single concentration of 16 (μg/mL). The active compounds from this screening were further tested against *M. tuberculosis* H$_{37}$Rv, *M. tuberculosis* Rif$^R$ and *M. tuberculosis* XDR-1 for Minimum Inhibitory Concentration (MIC) determination using a broth microdilution assay. Compounds demonstrating at least 90% inhibition in the primary screen were retested at lower concentrations by serial dilution against *M. tuberculosis* H$_{37}$Rv, *M. tuberculosis* Rif$^R$ and *M. tuberculosis* XDR-1 to determine the actual MIC, using the Nitrate Reductase Assay (NRA). The growth in the microtitre plate is indicated by the change in color to pink detected by the addition of NRA reagent. The MIC is defined as the lowest concentration of the compound showing no change in the color relative to controls. Rifampicin and Isoniazid were used as reference drugs. All these compounds have shown activity between 0.5→16 μg/mL.

TABLE 1

MIC values for the representative compounds

| S. No | Compound | MIC (μg/mL) | | |
|---|---|---|---|---|
| | | *M. tuberculosis* H$_{37}$Rv | *M. tuberculosis* Rif$^R$ | *M. tuberculosis* XDR-1 |
| 1 | 8a | 1.0 | 1.0 | 4.0 |
| 2 | 8b | —$^a$ | —$^a$ | —$^a$ |
| 3 | 8c | 1.0 | 2.0 | 4.0 |
| 4 | 8d | —$^a$ | —$^a$ | —$^a$ |
| 5 | 8e | 2.0 | 2.0 | 8.0 |
| 6 | 8f | 1.0 | 2.0 | 4.0 |
| 7 | 8g | 0.5 | 1.0 | 2.0 |
| 8 | 8h | —$^a$ | —$^a$ | —$^a$ |
| 9 | 9a | 2.0 | 4.0 | 4.0 |
| 10 | 9b | 2.0 | 4.0 | 8.0 |
| 11 | 9c | 1.0 | 2.0 | 4.0 |
| 12 | 9d | 2.0 | 4.0 | 8.0 |
| 13 | 9e | 2.0 | 2.0 | 8.0 |
| 14 | 9f | 2.0 | 4.0 | 8.0 |
| 15 | 9g | 1.0 | 2.0 | 4.0 |
| 16 | 9h | 2.0 | 2.0 | 8.0 |
| 17 | 10a | 1.0 | 4.0 | 4.0 |
| 18 | 10b | 2.0 | 4.0 | 8.0 |
| 19 | 10c | 1.0 | 1.0 | 4.0 |
| 20 | 10d | 2.0 | 2.0 | 8.0 |
| 21 | 10e | 2.0 | 2.0 | 8.0 |
| 22 | 10f | 4.0 | 8.0 | 16.0 |
| 23 | 10g | 2.0 | 4.0 | 4.0 |
| 24 | 10h | 2.0 | 4.0 | 8.0 |
| 26 | 11a* | 0.12 | —$^a$ | —$^a$ |
| 27 | 11b* | 0.8 | —$^a$ | —$^a$ |
| 28 | 11c* | 3.12 | —$^a$ | —$^a$ |
| 29 | 12a* | 3.13 | —$^a$ | —$^a$ |
| 30 | 12b* | 1.25 | —$^a$ | —$^a$ |
| 31 | 12c* | 2.5 | —$^a$ | —$^a$ |
| 32 | Isoniazid | 2.5 | —$^a$ | —$^a$ |
| 33 | Rifampicin | 0.5 | >128 | 2.0 |

—$^a$ refers to not tested;
*refers to literature values (11a, 11b, 11c, 12a, 12b and 12c, are reported in literature) (Tangallapally, R, P.; Yendapally, R.; Lee, R. E.; Hevener, K.; Jones, V. C.; Lenaerts, A. J. M.; McNeil, M. R.; Wang, Y.; Franzblau, S.; Lee, R. E. *J. Med. Chem.*, 2004, 47, 5276-5283.; Mamolo, M. G.; Zampieri, D.; Vio, L.; Fermeglia, m.; Ferrone, M.; Pricl, S,; Scialino, G. and Banfi, E. *Bioorg. Med. Chem.*, 2005, 13, 3797-3809).

ADVANTAGES OF THE INVENTION

1. The present invention provides phenyl nitro furfuryl linked piperidino oxadiazolone compounds of general formula A.
2. It also provides a process for the preparation of phenyl nitro furfuryl linked piperidino oxadiazolone compounds of general formula A.

The invention claimed is:
1. A compound of formula A or pharmaceutically acceptable salts thereof formula A wherein G is

X══H, F;
R══H, CH$_3$, C$_2$H$_5$, or ───CH$_2$C$_6$H$_5$.

2. The compound of formula A as claimed in claim 1, wherein said compound is selected from
  N2-4-[4-(5-Oxo-4,5-dihydro-1,3,4-oxadiazol-2-yl)piperidino]phenyl-5-nitro-2-furamide (8a);
  N2-4-[4-(4-Methyl-5-oxo-4,5-dihydro-1,3,4-oxadiazol-2-yl)piperidino]phenyl-5-nitro-2-furamide (8b);
  N2-4-[4-(4-Ethyl-5-oxo-4,5-dihydro-1,3,4-oxadiazol-2-yl)piperidino]phenyl-5-nitro-2-furamide (8c);
  N2-4-[4-(4-Benzyl-5-oxo-4,5-dihydro-1,3,4-oxadiazol-2-yl)piperidino]phenyl-5-nitro-2-furamide (8d);
  N2-3-Fluoro-4-[4-(5-oxo-4,5-dihydro-1,3,4-oxadiazol-2-yl)piperidino]phenyl-5-nitro-2-furamide (8e);
  N2-3-Fluoro-4-[4-(4-methyl-5-oxo-4,5-dihydro-1,3,4-oxadiazol-2-yl)piperidino]phenyl-5-nitro-2-furamide (8f);
  N2-4-[4-(4-Ethyl-5-oxo-4,5-dihydro-1,3,4-oxadiazol-2-yl)piperidino]-3-fluorophenyl-5-nitro-2-furamide (8g);
  N2-4-[4-(4-Benzyl-5-oxo-4,5-dihydro-1,3,4-oxadiazol-2-yl)piperidino]-3-fluorophenyl-5-nitro-2-furamide (8h);
  5-[1-(4-[(E)-1-(5-Nitro-2-furyl)methylidene]aminophenyl]-4-piperidyl]-2,3-dihydro-1,3,4-oxadiazol-2-one (9a);
  3-Methyl-5-[1-(4-[(E)-1-(5-nitro-2-furyl)methylidene]aminophenyl)-4-piperidyl]-2,3-dihydro-1,3,4-oxadiazol-2-one (9b);
  3-Ethyl-5-[1-(4-[(E)-1-(5-nitro-2-furyl)methylidene]aminophenyl)-4-piperidyl]-2,3-dihydro-1,3,4-oxadiazol-2-one (9c);
  3-Benzyl-5-[1-(4-[(E)-1-(5-nitro-2-furyl)methylidene]aminophenyl)-4-piperidyl]-2,3-dihydro-1,3,4-oxadiazol-2-one (9d);
  5-[1-(2-Fluoro-4-[(E)-1-(5-nitro-2-furyl)methylidene]aminophenyl)-4-piperidyl]-2,3-dihydro-1,3,4-oxadiazol-2-one (9e);
  5-[1-(2-Fluoro-4-[(E)-1-(5-nitro-2-furyl)methylidene]aminophenyl)-4-piperidyl]-3-methyl-2,3-dihydro-1,3,4-oxadiazol-2-one (9f);
  3-Ethyl-5-[1-(2-fluoro-4-[(E)-1-(5-nitro-2-furyl)methylidene]aminophenyl)-4-piperidyl]-2,3-dihydro-1,3,4-oxadiazol-2-one (9g);
  3-Benzyl-5-[1-(2-fluoro-4-[(E)-1-(5-nitro-2-furyl)methylidene]aminophenyl)-4-piperidyl]-2,3-dihydro-1,3,4-oxadiazol-2-one (9h);

5-[1-(4-[(5-Nitro-2-furyl)methyl]aminophenyl)-4-piperidyl]-2,3-dihydro-1,3,4-oxadiazol-2-one (10a);

3-Methyl-5-[1-(4-[(5-nitro-2-furyl)methyl]aminophenyl)-4-piperidyl]-2,3-dihydro-1,3,4-oxadiazol-2-one (10b);

3-Ethyl-5-[1-(4-[(5-nitro-2-furyl)methyl]aminophenyl)-4-piperidyl]-2,3-dihydro-1,3,4-oxadiazol-2-one (10c);

3-Benzyl-5-[1-(4-[(5-nitro-2-furyl)methyl]aminophenyl)-4-piperidyl]-2,3-dihydro-1,3,4-oxadiazol-2-one (10d);

5-[1-(2-Fluoro-4-[(5-nitro-2-furyl)methyl]aminophenyl)-4-piperidyl]-2,3-dihydro-1,3,4-oxadiazol-2-one (10e);

5-[1-(2-Fluoro-4-[(5-nitro-2-furyl)methyl]aminophenyl)-4-piperidyl]-3-methyl-2,3-dihydro-1,3,4-oxadiazol-2-one (10f);

3-Ethyl-5-[1-(2-fluoro-4-[(5-nitro-2-furyl)methyl]aminophenyl)-4-piperidyl]-2,3-dihydro-1,3,4-oxadiazol-2-one (10g);

3-Benzyl-5-[1-(2-fluoro-4-[(5-nitro-2-furyl)methyl]aminophenyl)-4-piperidyl]-2,3-dihydro-1,3,4-oxadiazol-2-one (10h); or a pharmaceutically acceptable salt thereof.

3. The compound of formula A as claimed in claim 1, wherein said compound is selected from 8a 8b 8c 8d 8e 8f 8g 8h 9a 9b 9c 9d

9e

9f

9g

9h

10a

10b

10c

10d

10e

10f

10g

10h or a pharmaceutically acceptable salt thereof.

4. A pharmaceutical composition comprising an anti-tuberculosis effective amount of compound of formula A as claimed in claim 1 or a pharmaceutically acceptable salt thereof.

5. A process of treating *Mycobacterium tuberculosis* H37Rv, *Mycobacterium tuberculosis* RifR, or *Mycobacterium tuberculosis* XDR-1, infection in a patient comprising administering a therapeutically effective amount of a compound of formula A as claimed in claim 1, for a period of 3-4 days.

6. A process for the preparation of the compounds of formula A or pharmaceutically acceptable salts thereof as claimed in claim 1 wherein the said process comprises the steps of:

i. heating methyl 4-piperidinecarboxylate (2) with compounds of general formula 1(a-b) in dimethylsulphoxide and in the presence of base selected from $K_2CO_3$ or $Na_2CO_3$ for a period in the range of 8 to 10 h at temperature ranging between 70 to 80° C. to obtain compound of general formula 3(a-b)

1(a-b)

1a X = H, 1b X = F

2

2

3a X = H, 3b X = F, ii. treating the compounds of formula 3(a-b) as obtained in step i. with NH$_2$NH$_2$.H$_2$O in solvent selected from ethanol or 2-propanol under refluxing temperature ranging between 65 to 70° C. for a period in the range of 12 to 24 h to obtain hydrazide of formula 4(a-b).

4a X = H, 4b X = F iii. adding N,N-dimethylcarbamylchloride to hydrazide 4(a-b) as obtained in step (ii) in pyridine at temperature ranging between 25 to 27° C. and followed by refluxing at temperature ranging between 85 to 90° C. for 2 to 3 h to obtain the compounds of general formula 5(a-b).

5a X = H
5b X = F iv. reading the compound of formula 5(a-b) with halides selected from alkyl halides or benzyl bromide in N,N-dimethylformamide (DMF) at a temperature ranging between 25° C. to 27° C. for a period in the range of 10 to 12 h or in acetone at refluxing temperature in the range of 65 to 70° C. for 12 to 24 h to obtain the compounds of general formula 6(a-f).

X = H, F;
R = CH$_3$, C$_2$H$_5$, CH$_2$C$_6$H$_5$;

6a X = H, R = CH$_3$;
6b X = H, R = C$_2$H$_5$;
6c X = H, R = CH$_2$C$_6$H$_5$;
6d X = F, R = CH$_3$;
6e X = F, R = C$_2$H$_5$;
6f X = F, R = CH$_2$C$_6$H$_5$ v. reducing the compound of formula 5(a-b) as obtained in step iii or 6(a-f) as obtained in step iv by SnCl$_2$.2H$_2$O or Fe powder and two drops of conc HCl in methanol at refluxing temperature in the range of 65 to 70° C. for a period in the range of 4 to 6 h or Zinc in acetic acid at room temperature (25 to 27° C.) for 4 to 5 h to obtain the compound of general formula (7a-h).

X = H, F; R = H, CH$_3$, C$_2$H$_5$, CH$_2$C$_6$H$_5$;
7a X = H, R = H;
7b X = H, R = CH$_3$;
7c X = H, R = C$_2$H$_5$;
7d X = H, R = CH$_2$C$_6$H$_5$;
7e X = F, R = H;
7f X = F, R = CH$_3$;
7g X = F, R = C$_2$H$_5$;
7h X = F, R = CH$_2$C$_6$H$_5$;

vi. reacting the compound of formula 7(a-h) with 5-nitro2-furanoic acid, 1-Ethyl-3-(3-dimethylaminopropyl)carbodiimide) (EDCI) and Hydroxybenzotriazole (HOBT) in N,N-dimethylformamide (DMF) at temperature ranging between 25° C. to 27° C. for a period in the range of 3 to 4 h to obtain final compound of general formula 8(a-h).

X = H, F;
R = H, CH$_3$, C$_2$H$_5$, Bn;

vii. reacting the compound (7a-h) with 5-nitro2-furaldehyde in the presence of catalytic amount of acid selected from CH$_3$COOH or H$_2$SO$_4$ in solvent selected from methanol or ethanol at a temperature ranging between 0° C. to 5° C. for a period in the range of 10 to 12 h to obtain the compounds of general formula 9(a-h).

X = H, F; R = H, CH$_3$, C$_2$H$_5$, CH$_2$C$_6$H$_5$;

viii. reducing the compound (9a-h) by reducing agent selected from sodium cyanoborohydride, or sodium triacetoxyborohydride in the presence of catalytic amount of CH$_3$COOH in solvent selected from methanol or ethanol at a temperature ranging between 0 to 5° C. for a period in the range of 10 to 12 h to obtain the compounds of general formula (10(a-h).

10(a-h)

X = H, F; R = H, CH₃, C₂H₅, CH₂C₆H₅;

ix. purifying the compounds of formula 8(a-h) to 10(a-h) as obtained in step vi, vii and viii by column chromatography to obtain the compounds of general formula A.

x. converting the compound of general formula A to their salt.

7. A process as claimed in step (ix) of claim 6, wherein solvent used are selected from a group consisting of ethyl acetate, hexane, chloroform or methanol.

8. A process as claimed in claim 6, wherein the pharmaceutically acceptable salt of the compound of general formula A is selected form a group consisting of hydrochloride, hydrobromide, tartarate, succinate, maleate.

9. A process as claimed in claim 6, wherein the representative pharmaceutically acceptable salt of the compound of general formula A comprising:

5-(1-(4-(1-(((5-nitro-2-furyl)methyl)ammonio)phenyl)-4-piperidyl)-2,3-dihydro-1,3,4-oxadiazol-2-one chloride 3-methyl-5-(1-(4-(1-((5-nitro-2-furyl)methyl)ammonio)phenyl)-4-piperidyl)-2,3-dihydro-1,3,4-oxadiazol-2-one chloride 3-ethyl-5-(1-(4-(1-(5-nitro-2-furyl)methyl)ammonio)phenyl)-4-piperidyl)-2,3-dihydro-1,3,4-oxadiazol-2-one chloride 3-benzyl-5-(1-(4-(1-((5-nitro-2-furyl)methyl)ammonio)phenyl)-4-piperidyl)-2,3-dihydro-1,3,4-oxadiazol-2-one chloride 5-(1-(2-fluoro-4-(1-((5-nitro-2-furyl)methyl)ammonio)phenyl)-4-piperidyl)-2,3-dihydro-1,3,4-oxadiazol-2-one chloride 5-(1-(2-fluoro-4-(1-((5-nitro-2-furyl)methyl)ammonio)phenyl)-4-piperidyl)-3-methyl-2,3-dihydro-1,3,4-oxadiazol-2-one chloride 3-ethyl-5-(1-(2-fluoro-4-(1-((5-nitro-2-furyl)methyl)ammonio)phenyl)-4-piperidyl)-2,3-dihydro-1,3,4-oxadiazol-2-one chloride 3-benzyl-5-(1-(2-fluoro-4-(1-((5-nitro-2-furyl)methyl)ammonio)phenyl)-4-piperidyl)-2,3-dihydro-1,3,4-oxadiazol-2-one chloride.

* * * * *